(12) United States Patent
Yoshida et al.

(10) Patent No.: US 8,283,457 B2
(45) Date of Patent: Oct. 9, 2012

(54) NUCLEIC ACID MOLECULE CAPABLE OF BINDING TO RABBIT-DERIVED IGG ANTIBODY

(75) Inventors: Yoshihito Yoshida, Koto-ku (JP); Makio Furuichi, Koto-ku (JP); Iwao Waga, Koto-ku (JP); Hiroshi Mizuno, Koto-ku (JP)

(73) Assignee: NEC Soft, Ltd., Tokyo (JP)

( * ) Notice: Subject to any disclaimer, the term of this patent is extended or adjusted under 35 U.S.C. 154(b) by 311 days.

(21) Appl. No.: 12/516,293

(22) PCT Filed: Nov. 22, 2007

(86) PCT No.: PCT/JP2007/072691
§ 371 (c)(1),
(2), (4) Date: Jan. 13, 2010

(87) PCT Pub. No.: WO2008/062882
PCT Pub. Date: May 29, 2008

(65) Prior Publication Data
US 2010/0222559 A1    Sep. 2, 2010

(30) Foreign Application Priority Data
Nov. 24, 2006  (JP) .................................. 2006-317113

(51) Int. Cl.
*C07H 21/02* (2006.01)
(52) U.S. Cl. .................................................... 536/23.1
(58) Field of Classification Search .................. None
See application file for complete search history.

(56) References Cited

U.S. PATENT DOCUMENTS
2003/0049644 A1  3/2003  Rabin et al.

FOREIGN PATENT DOCUMENTS

| | | |
|---|---|---|
| EP | 1918372 A1 | 5/2008 |
| JP | 6-508022 A | 9/1994 |
| JP | 2003-506024 A | 2/2003 |
| WO | 92/14843 A1 | 9/1992 |
| WO | 01/09159 A1 | 2/2001 |
| WO | 2004/098384 A2 | 11/2004 |
| WO | 2007/004748 A1 | 1/2007 |
| WO | 2007/109067 A2 | 9/2007 |

OTHER PUBLICATIONS

Kim et al., "Specific modulation of the anti-DNA autoantibody-nucleic acids interaction by the high affinity RNA aptamer", Biochemical and Biophysical Research Communications, vol. 300, No. 2, pp. 516-523, Jan. 10, 2003.
Stadtherr et al., "An Aptamer-Based Protein Biochip", Analytical Chemistry, vol. 77, No. 11, pp. 3437-3443, Jun. 1, 2005.
Famulok, et al., "Aptamers as Tools in Molecular Biology and Immunology", Current Topics in Microbiology and Immunology, Springer, Berlin, vol. 243, pp. 123-136, 1999.
Yoshida et al., "Rabbit antibody detection with RNA aptamers", Analytical Biochemistry, vol. 375, No. 2, pp. 217-222, Jan. 9, 2008.
Sakai et al., "RNA aptamers specifically interact with the Fc region of mouse immunoglobulin G", Nucleic Acids Symposium Series, No. 52, pp. 487-488, Sep. 8, 2008.
Yoshida et al., "Antibody-specific aptamer-based PCR analysis for sensitive protein detection", Analytical and Bioanalytical Chemistry, vol. 395, No. 4, pp. 1089-1096, Aug. 25, 2009.
Miyakawa et al., "Structural and molecular basis for hyperspecificity of RNA aptamer to human immunoglobulin G", RNA, vol. 14, No. 6, pp. 1154-1163, Jun. 1, 2008.
Sugiyama et al., "Crystallization and preliminary X-ray diffraction studies of an RNA aptamer in complex with the human IgG Fc fragment", Acta Crystallographica Section F, vol. 64, No. Pt 10, pp. 942-944, Oct. 1, 2008.
Michael Zuker et al., "On Finding All Suboptimal Folding of an RNA Molecule," Science, 1989 pp. 48-52, vol. 244.
Sotiris Missailidis et al., "Selection of aptamers with high affinity and high specificity against C595, an anti-MUCl IgG3 monoclonal antibody, for antibody targeting," Journal of Immunological Methods, 2005, pp. 45-62, vol. 296.
Shaun D. Mendonsa et al. "In Vitro Selection of High-Affinity DNA Ligands for Human IgE Using Capillary Electrophoresis," Analytical Chemistry, 2004, pp. 5387-5392, vol. 76, No. 18.

*Primary Examiner* — Ruixiang Li
(74) *Attorney, Agent, or Firm* — Sughrue Mion, PLLC

(57) ABSTRACT

The present invention provides a nucleic acid molecule having an ability to bind to a rabbit anti-mouse IgG antibody, which can be prepared more easily than an antibody and has a binding ability equal to or higher than that of an antibody. The nucleic acid molecule according to the present invention may have the sequences set forth in SEQ ID NOS: 1 to 5. The nucleic acid molecule according to the present invention may be a nucleic acid having an ability to bind to a rabbit IgG antibody, which substantially has homology to its sequence. The nucleic acid molecule according to the present invention may have a binding constant ($K_D$) of $1.18 \times 10^{-7}$ (M) or less to the rabbit IgG antibody.

6 Claims, 5 Drawing Sheets

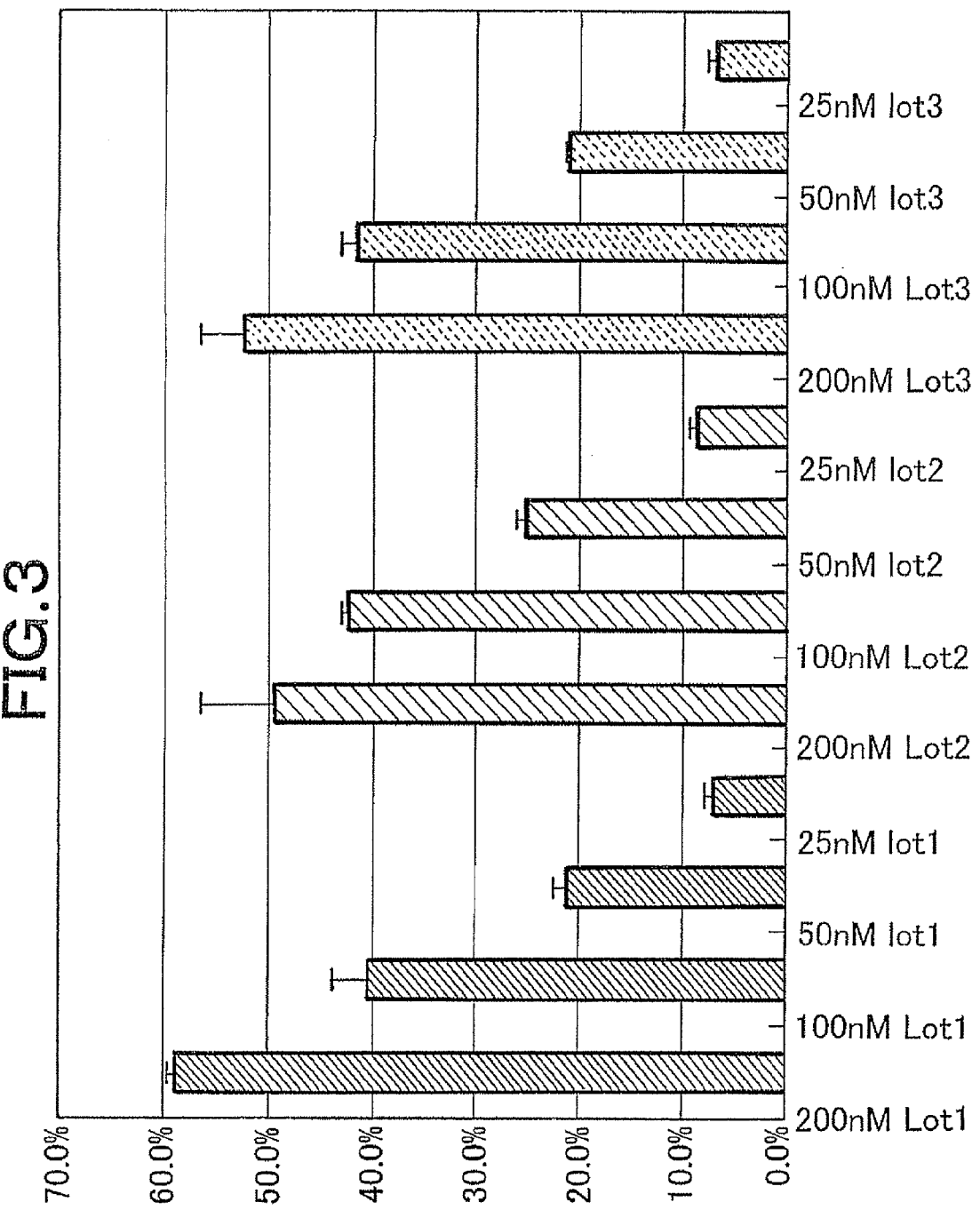

SEQUENCE LISTING

<160> NUMBER OF SEQ ID NOS: 10

<210> SEQ ID NO 1
<211> LENGTH: 96
<212> TYPE: RNA

<213> ORGANISM: Artificial
<220> FEATURE:
<223> OTHER INFORMATION: R2

<400> SEQUENCE: 1
aguaauacga cucacuauag ggagaauucc gaccagaaga aguucgauac gccgugggu    60 gacguuggcu gcccuuuccu cucccuccu ucuucu                              96

<210> SEQ ID NO 2
<211> LENGTH: 95
<212> TYPE: RNA
<213> ORGANISM: Artificial
<220> FEATURE:
<223> OTHER INFORMATION: R10

<400> SEQUENCE: 2
aguaauacga cucacuauag ggagaauucc gaccagaagu uuuuaaaccg cgccuuggaa    60
gcguacguug gccuuccuc ucuccuccuu cuucu                               95

<210> SEQ ID NO 3
<211> LENGTH: 91
<212> TYPE: RNA
<213> ORGANISM: Artificial
<220> FEATURE:
<223> OTHER INFORMATION: R11

<400> SEQUENCE: 3
aguaauacga cucacuauag ggagaauucc gaccagaagc aaauugccgg gccuuggaag    60
ccaagucgcu uccucucuc cuccuucuuc u                                   91

<210> SEQ ID NO 4
<211> LENGTH: 92
<212> TYPE: RNA
<213> ORGANISM: Artificial
<220> FEATURE:
<223> OTHER INFORMATION: R15

<400> SEQUENCE: 4
aguaauacga cucacuauag ggagaauucc gaccagaagc gcaagccggc ccuuggaagg    60
cuagucgguc uuuccucucu ccuccuucuu cu                                 92

<210> SEQ ID NO 5
<211> LENGTH: 92
<212> TYPE: RNA
<213> ORGANISM: Artificial
<220> FEATURE:
<223> OTHER INFORMATION: R18

<400> SEQUENCE: 5
aguaauacga cucacuauag ggagaauucc gaccagaagu ucgauacgcc gugggugac    60 guuggcuacc uuuccucucu ccuccuucuu cu                                 92

<210> SEQ ID NO 6
<211> LENGTH: 93
<212> TYPE: DNA
<213> ORGANISM: Artificial
<220> FEATURE:
<223> OTHER INFORMATION: RNA pool
<220> FEATURE:
<221> NAME/KEY: misc_feature
<222> LOCATION: (40)..(69)
<223> OTHER INFORMATION: n is a, c, g, or t

<400> SEQUENCE: 6

-continued

```
agtaatacga ctcactatag ggagaattcc gaccagaagn nnnnnnnnnn nnnnnnnnnn    60
nnnnnnnnnc ctttcctctc tcctccttct tct                                 93

<210> SEQ ID NO 7
<211> LENGTH: 93
<212> TYPE: RNA
<213> ORGANISM: Artificial
<220> FEATURE:
<223> OTHER INFORMATION: RNA pool
<220> FEATURE:
<221> NAME/KEY: misc_feature
<222> LOCATION: (40)..(69)
<223> OTHER INFORMATION: n is a, c, g, or u

<400> SEQUENCE: 7
aguaauacga cucacuauag ggagaauucc gaccagaagn nnnnnnnnnn nnnnnnnnnn    60
nnnnnnnnnc cuuccucuc uccuccuucu ucu                                  93

<210> SEQ ID NO 8
<211> LENGTH: 39
<212> TYPE: DNA
<213> ORGANISM: Artificial
<220> FEATURE:
<223> OTHER INFORMATION: primer for forward

<400> SEQUENCE: 8
agtaatacga ctcactatag ggagaattcc gaccagaag                           39

<210> SEQ ID NO 9
<211> LENGTH: 24
<212> TYPE: DNA
<213> ORGANISM: Artificial
<220> FEATURE:
<223> OTHER INFORMATION: primer for reverse

<400> SEQUENCE: 9
cctttcctct ctcctccttc ttct                                           24

<210> SEQ ID NO 10
<211> LENGTH: 24
<212> TYPE: DNA
<213> ORGANISM: Artificial
<220> FEATURE:
<223> OTHER INFORMATION: primer for RT-PCR

<400> SEQUENCE: 10
agaagaagga ggagagagga aagg                                           24
```

US 8,283,457 B2

NUCLEIC ACID MOLECULE CAPABLE OF BINDING TO RABBIT-DERIVED IGG ANTIBODY

TECHNICAL FIELD

The present invention relates to a nucleic acid molecule having an ability to bind to a rabbit IgG antibody.

BACKGROUND ART

Oligonucleotides such as DNA and RNA have been considered to mainly have functions as molecular species involved mainly in protein synthesis, and have attracted attention since phenomena such as in a ribozyme or RNAi, in which nucleic acid molecules can interact directly with molecular species such as proteins or macromolecules, thereby regulating functions of such molecular species, have been discovered. In particular, an aptamer has recently attracted attention as a nucleic acid capable of binding directly to a molecular species such as a protein, thereby modifying the function of the protein. A large number of novel aptamers have been obtained for the purpose of applying them to a pharmaceutical or the like.

On the other hand, an antibody belonging to a class such as IgG, which is derived from a laboratory animal such as a mouse, rat or rabbit, collectively refers to a proteinous substance capable of binding, in a binding mode such as hydrogen bond, to a high-molecular compound such as a protein or a antibody capable of forming an antigen-antibody complex. Such an antibody is widely used in the field of medicine (for example, as a diagnostic agent) as an antibody that specifically binds to, for example, an antibody in an antigen-antibody complex.

However, although such an antibody is useful in that it has a specific activity for the counterpart antigen, various problems have been mentioned in preparation of the antibody. For example, in order to prepare antibodies, after an antigen is repeatedly injected into an animal to be immunized such as a mouse, rat or rabbit, thereby inducing the immune-reaction, it is required to obtain a desired fraction having an ability to bind to the antigen from serum etc. Therefore, such a process of preparation is very disadvantageous in terms of laborsaving and costs. Moreover, the antibody has nonspecific binding properties to various proteins or polypropylene or polyethylene containers other than the antigen that the antibody specifically binds to, and is also disadvantageous in terms of ease in handling. Furthermore, preparation of antibodies requires use of immune animals as described above, and such use of immune animals is not preferable from the viewpoint of animal protection.

When an antibody is used as a secondary antibody for the above-mentioned diagnostic agent, the antibody needs to be prepared as a complex with a labeling compound such as a peroxidase in order to spectrophotometrically detect the degree of binding to an antigen-antibody complex. However, preparation of such a complex further makes the process complex besides preparation of the secondary antibody.

Accordingly, a molecular species capable of binding specifically to an antigen has been sought as an alternative to an antibody.

Non-Patent Document 1: M. Zuker, Science, vol. 244, pp 48-52, 1989

DISCLOSURE OF THE INVENTION

Problems to be Solved by the Invention

The present invention was achieved in view of the above-described problems. The object of the present invention is to provide a nucleic acid molecule having an ability to bind to a rabbit anti-mouse IgG antibody which can be prepared more easily than an antibody and which has a binding ability equal to or higher than that of an antibody.

Means for Solving the Problems

The nucleic acid molecule according to the present invention is characterized by possession of an ability to bind to a rabbit IgG antibody.

Effect of the Invention

The nucleic acid molecule according to the present invention is useful as a substance capable of binding to a rabbit IgG antibody.

BRIEF DESCRIPTION OF THE DRAWINGS

FIG. 1-2 shows a sensorgram obtained in Example 4-2.
FIG. 1-3 shows a sensorgram obtained in Example 4-3.
FIG. 2 shows the binding strength obtained in Example 6.
FIG. 3 shows the binding strength obtained in Example 7.

BEST MODE FOR CARRYING OUT THE INVENTION

Figure 1:
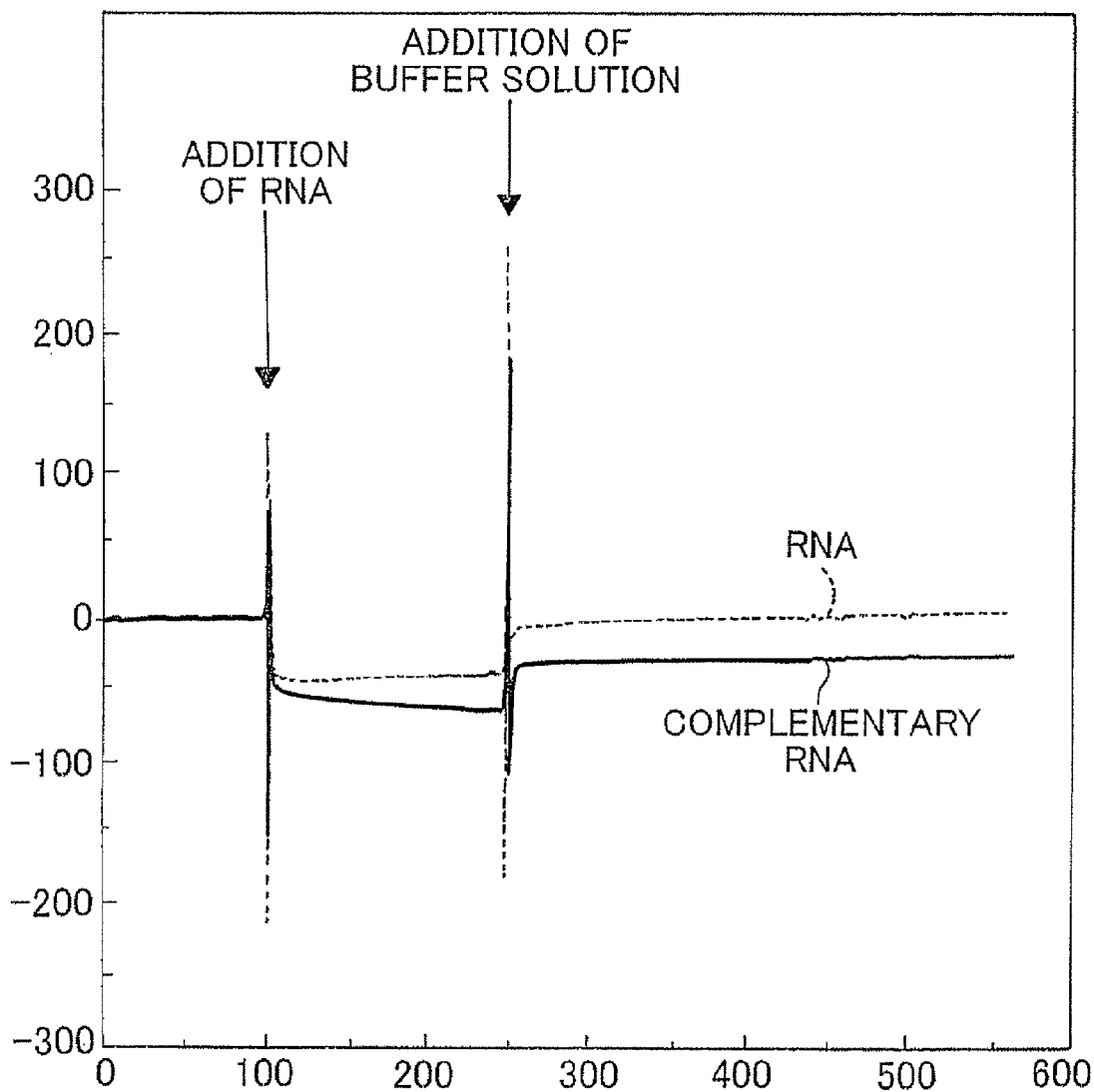
FIG. 1-1 shows a sensorgram obtained in Example 4-1.

In the present invention, the nucleic acid molecule is not particularly limited as long as the nucleic acid molecule is a nucleotide including typical nucleic acids such as adenine (A), guanine (G), cytosine (C), thymine (T) and uracil (U), and the nucleic acid molecule includes ssDNA, ssRNA, dsDNA and dsRNA without being limited by the number of strands or by the presence or absence of modifications on the nucleic acid.

In the present invention, the "rabbit IgG antibody" collectively refers to an antibody present in an IgG fraction in serum obtained by inducing an immunoreaction in rabbits with a certain antigen.

It is preferable that the binding constant ($K_D$) of the nucleic acid molecule of the present invention to a rabbit IgG antibody be $1.18 \times 10^{-7}$ (M) or less.

The nucleic acid molecule according to the present invention is a nucleic acid having an ability to bind to a rabbit IgG antibody, and preferably substantially has homology to the sequence of the nucleic acid. In the present invention, the phrase "substantially has homology" means having 70% or higher, most preferably 80% or higher, and more preferably 90%, 95% or 99% or higher homology in the primary sequence.

The nucleic acid molecule according to the present invention is a nucleic acid having an ability to bind to a rabbit IgG antibody, and preferably has a substantially identical predicted structure or structural motif. In the present invention, the phrase "has a substantially identical predicted structure or structural motif" means having a certain identity which is found in a sequence group consisting of a plurality of sequences by using a program for predicting a secondary structure and a motif in the secondary structure with respect to a nucleic acid sequence. With regard to this certain identity, there may preferably be a 70% or higher homology between the sequences to be compared and contrasted with each other. By substantially having a certain identity, the nucleic acid molecule of the present invention improves the ability to bind to a rabbit IgG antibody. For example, such a program may be the mfold program developed by Dr. Zuker which is described in Non-Patent Document 1.

<Method of Producing the Nucleic Acid Molecule According to the Present Invention>

The nucleic acid molecule according to the present invention can be produced according to a SELEX method (Systematic Evolution of Ligands by Exponential Enrichment) using a so-called RNA pool and a rabbit IgG antibody as a target substance. Hereinafter, the method of preparing the nucleic acid molecule of the present invention according to the SELEX method will be described.

(Method of Producing the Nucleic Acid Molecule of the Present Invention According to the SELEX Method)

According to a method based on the SELEX method, an RNA pool is reacted with a target substance, the resulting RNA pool-target substance complexes are recovered, and then, only the RNA pool associated with formation of the complexes is recovered from the complexes, thereby producing the nucleic acid molecule of the present invention.

The RNA pool refers to a mixture of nucleic acids that collectively mean nucleic acid sequences each having a region (hereinafter, referred to as "random region") wherein about 20 to 120 bases selected from the group consisting of A, G, C and U are linked. Accordingly, the RNA pool contains a plurality of $4^{20}$ to $4^{120}$ ($10^{12}$ to $10^{72}$) nucleic acid sequences, and preferably contains $4^{30}$ to $4^{60}$ ($10^{18}$ to $10^{36}$) nucleic acid sequences.

The structure of the RNA pool is not limited as long as the structure includes a random region. If the nucleic acid molecule according to the present invention is produced based on the SELEX method, it is preferable that a primer region, which is used in the PCR or the like as described below, or a region recognized by a DNA-dependent RNA polymerase be present at the 5' end and/or 3' end of the random region. For example, the RNA pool may have a structure wherein, in the direction of from the 5' end to 3' end, a region (e.g. T7 promoter) which is recognized by a DNA-dependent RNA polymerase (hereinafter, referred to as "RNA polymerase-recognition region") and a primer region for a DNA-dependent DNA polymerase (hereinafter, referred to as "5'-end primer region") are combined with each other; the random region is linked to the 3' end of 5'-end primer region; and a primer region for a DNA-dependent DNA polymerase (hereinafter, referred to as "3'-end primer region") is further linked to the 3' end of the random region. Besides these regions, the RNA pool may have a known region that assists the nucleic acid molecule in binding to the target substance. A part of the random region of the RNA pool may have the same sequence as in other RNA pools.

An initial pool wherein U in the random region of the RNA pool is replaced by T may be used as a template to amplify the nucleic acid sequences based on the PCR method, and then, the resulting PCR product may be reacted with a DNA-dependent RNA polymerase such as T7 polymerase, thereby preparing the RNA pool.

Then, the RNA pool synthesized in this manner is bound, via an intermolecular force such as hydrogen bonding, to a rabbit antibody of the target substance. As the method for binding the RNA pool to the target substance, a method wherein the RNA pool and the target substance are incubated for a predetermined time in a buffer solution capable of maintaining functions such as binding properties to the target substance can be mentioned. In this manner, RNA pool-target substance complexes are formed in the buffer solution.

Then, the RNA pool-target substance complexes formed in this manner are recovered. The buffer solution contains not only such complexes but also the RNA pool and target substance that were not associated with formation of the complexes. With regard to the method of recovering the complexes, the RNA pool that is not associated with formation of the complexes may be removed from the buffer solution in order to recover the nucleic acid molecules having an ability to bind to the target substance. Such a method includes a method of using the difference in the adsorptive properties between the target substance and the RNA pool, or a method of using the difference between the molecular weight of the complex and that of the RNA pool.

As an example of the method of using the difference in the adsorptive properties between the target substance and the RNA pool, the following method can be mentioned. That is, in the method, a membrane (e.g. nitrocellulose) having an ability to adsorb the target substance is used to filter the buffer solution containing the RNA pool-target substance complexes, thereby adsorbing the RNA pool-target substance complexes onto the membrane. Then, from the RNA pool-target substance complexes remaining on the membrane, the RNA pool that was associated with formation of the complexes is then recovered by, for example, dissolution of the bonding between the RNA pool and the target substance in the complexes.

On the other hand, as an example of the method of using the difference between the molecular weight of the complex and that of the RNA pool, the following method can be mentioned. That is, in the method, a carrier such as agarose gel that has pores that the RNA pool can pass through and that the RNA pool-target substance complexes cannot pass through is used to electrically separate the RNA pool-target substance complexes and the RNA pool from each other. Then, the RNA pool that was associated with formation of the complexes is recovered from the complexes.

The recovered RNA pool associated with formation the complexes is then subjected to a reverse transcription reaction to prepare a single-stranded complementary strand DNA, and then, the double-stranded DNA is amplified based on the PCR method. The method for this DNA amplification includes a method of using the 5'-end primer region, 3'-end primer region and the RNA polymerase-recognition region included in the RNA pool. For example, a DNA fragment complementary to the 3'-end primer region of the RNA pool is used as a primer to prepare the cDNA based on a reverse transcription reaction with an RNA-dependent DNA polymerase such as avian myeloblastosis virus-derived reverse transcriptase (AMV reverse transcriptase), and then, the cDNA is subjected to PCR with a DNA-dependent DNA polymerase by utilizing the 5'- and 3-end primer regions included in the cDNA. Then, the resulting PCR product is subjected to an in vitro transcription reaction with a DNA-dependent RNA polymerase by utilizing the RNA polymerase-recognition region included in the PCR product. In this manner, the RNA pool may be amplified.

By using the above-amplified RNA pool associated with formation of the complexes and the target substance, the above-described method of forming the RNA pool-target substance complexes and the subsequent methods are repeated, whereby the nucleic acid molecule having an ability to bind a rabbit IgG antibody as the target substance can be finally obtained.

(Method of Producing the Nucleic Acid Molecule of the Present Invention According to Other Methods)

The nucleic acid molecule can be synthesized by a variety of methods known in the art. For example, the nucleic acid molecule of the present invention may be a nucleic acid molecule that is chemically synthesized starting from a terminal base by using a DNA synthesizer with dNTP as a material.

EXAMPLES

Example 1

The initial pool set forth in SEQ ID NO: 6 was synthesized with a DNA synthesizer (334 DNA synthesizer manufactured by Applied Biosystems). This initial pool (500 nM), primer 1 (SEQ ID NO: 8), primer 2 (SEQ ID NO: 9), and 2.5 U of a DNA polymerase (trade name: Ex-Taq, manufactured by Takara Bio Inc.) were used to prepare a cDNA consisting of the initial pool and a sequence complementary to the initial pool. Then, the above-obtained cDNA and a T7 RNA polymerase (trade name: Ampliscribe, manufactured by EPICENTRE) were used to conduct a transcription reaction, thereby preparing an RNA pool (SEQ ID NO: 7).

20 µM of the RNA pool and 1 µM of a rabbit anti-mouse IgG antibody (hereinafter, referred to as a "target substance") manufactured by Chemicon were incubated in a binding buffer (50 mM HEPES, pH 7.4, 150 mM NaCl, 5 mM $MgCl_2$) at room temperature for twenty minutes. The resulting mixture was introduced into a nitrocellulose membrane fixed to a pop-top holder, and was filtered through it. Then, the membrane was washed with 1 mL of the binding buffer. Thereafter, this membrane was immersed in 300 µL of an eluent (50 mM HEPES, pH 7.4, 150 mM NaCl, 7 M urea), and was heated to 90° C. for five minutes. The resulting solution was subjected to precipitation with ethanol, thereby obtaining oligonucleotides.

Thereafter, the whole volume of the oligonucleotides, primer 3 (SEQ ID NO: 10), AMV transcriptase (10 U, manufactured by Roche Diagnostics) were used to conduct a reverse transcription reaction at 42° C. for 1 hour.

The whole volume of the reaction product, 2.5 U of a DNA polymerase (trade name: Ex-Taq, manufactured by Takara Bio Inc.), 30 nM of primer 1 (SEQ ID NO: 8) and primer 2 (SEQ ID NO: 9) were used to conduct twelve cycles of PCR where each cycle includes steps of 90° C.×50 seconds, 53° C.×70 seconds and 74° C.×50 seconds in this order. The resulting solution was subjected to ethanol precipitation, thereby obtaining a double-stranded DNA product.

This double-stranded DNA product was dissolved in 8 µL of RNase-free water, and 4 µL of the resulting solution and 2 µL of T7 RNA polymerase (trade name: Ampliscribe, manufactured by EPICENTRE) were used to conduct in vitro transcription thereby obtaining an in vitro transcript. The process that has so far been performed is referred to as one cycle.

Ten cycles of the above-described process were carried out using the in vitro transcript as the RNA pool. As a result, the RNAs set forth in SEQ ID NOS: 1 to 5 were obtained.

Example 2

The RNAs (20 nM each) set forth in SEQ ID NOS: 1 to 5, and 100 nM of target substance were incubated in a binding buffer at room temperature for twenty minutes. With respect to the resulting mixture, the binding strength was measured based on the method described in "Binding Experiment" below. The results are shown in Table 1. The numerical values in Table 1 are shown in percentage relative to radiation intensity (=100%) of the radiolabeled in vitro transcript before the "Binding Experiment".

TABLE 1

| SEQ ID NO. | Binding strength (%) |
|---|---|
| SEQ ID NO. 1 | 19.1 |
| SEQ ID NO. 2 | 24.6 |
| SEQ ID NO. 3 | 20.9 |
| SEQ ID NO. 4 | 23.4 |
| SEQ ID NO. 5 | 58.1 |

Example 3

The binding activity of each of the RNAs in SEQ ID NOS: 1 to 5 to the target substance was measured with Biosensor Biacore 3000 (manufactured by Biacore) utilizing surface plasmon resonance based on the following conditions.

At first, those obtained by linking twenty-four adenine bases to the 5' end of RNAs of SEQ ID NOS: 1 to 5 were prepared as ligands, based on a conventional method. Deoxythymines of twenty-four-base length whose 5' end was biotin-labeled were immobilized on Sensor Chip SA (manufactured by Biacore), and then, the prepared RNAs were bound to the deoxythymines. 3.125 nM, 6.25 nM, 12.5 nM, 25 nM, 50 nM or 100 nM of the target substance was added thereto at a flow rate of 20 µL/min for two minutes, whereby the binding state of the measured object was observed, and then, the dissociation state was observed over three minutes. The reaction was carried out at 25° C. With respect to the binding reaction curve at each concentration of the target substance obtained in this observation, the rate constant and the dissociation constant (ka ($Ms^{-1}$), kd ($s^{-1}$) and KD (M)) were calculated, respectively. These binding constants were subjected to $\chi$ (chi)-square test. The results are shown in Table 2.

TABLE 2

| | Binding strength | | | |
|---|---|---|---|---|
| SEQ ID NO. | ka ($Ms^{-1}$) | kd ($s^{-1}$) | KD (M) | $\chi^2$ |
| SEQ ID NO. 1 | $5.64 \times 10^4$ | $7.3 \times 10^{-7}$ | $1.3 \times 10^{-11}$ | 0.45 |
| SEQ ID NO. 2 | $2.84 \times 10^4$ | $1.47 \times 10^{-3}$ | $5.15 \times 10^{-8}$ | 2.07 |
| SEQ ID NO. 3 | $2.22 \times 10^4$ | $2.63 \times 10^{-3}$ | $1.18 \times 10^{-7}$ | 9.88 |
| SEQ ID NO. 4 | $7.62 \times 10^4$ | $7.81 \times 10^{-3}$ | $1.03 \times 10^{-7}$ | 1.81 |
| SEQ ID NO. 5 | $2.54 \times 10^4$ | $3.6 \times 10^{-7}$ | $1.47 \times 10^{-11}$ | 0.39 |

Example 4-1

A sensorgram was obtained by utilizing surface plasmon resonance in the same manner as in Example 3 except that the RNA in SEQ ID NO: 5 and an RNA having a sequence complementary to the RNA were used in place of the RNAs in SEQ ID NOS: 1 to 5; 10000 RU of glutathione-S-transferase (GST) (1 RU is an unit corresponding to an amount that cause a change in mass of 1 pg per unit square in millimeter) was used in place of 3.125 nM, 6.25 nM, 12.5 nM, 25 nM, 50 nM and 100 nM of the target substance; and the binding time was changed from two minutes to 2.5 minutes. The results are shown in FIG. 1-1. In FIG. 1-1, the ordinate refers to the amount of the bound target substance (unit: RU) while the abscissa refers to the time (sec).

Example 4-2

Figures 1, 2:
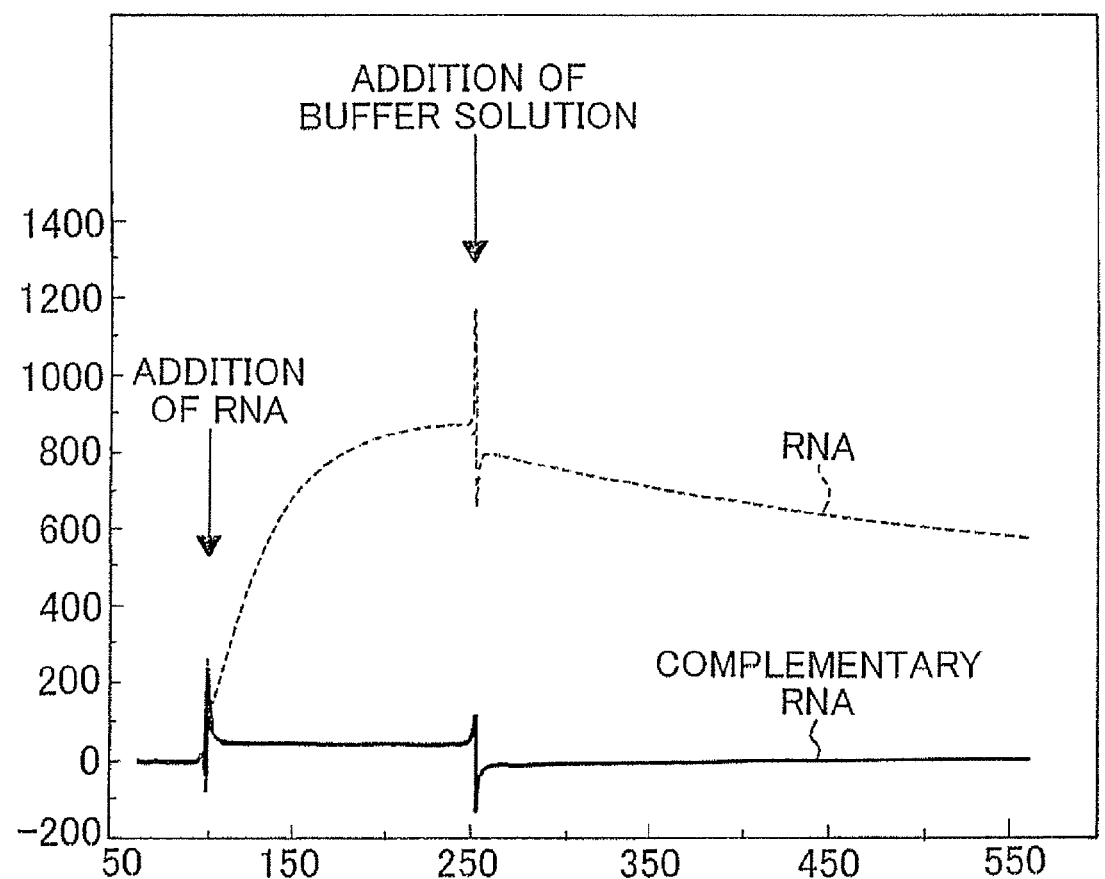

A sensorgram was obtained by utilizing surface plasmon resonance in the same manner as in Example 4-1 except that a mixture of 10000 RU of GST and 10000 RU of anti-GST antibody (rabbit IgG, manufactured by Chemicon) was used in place of 10000 RU of GST. The results are shown in FIG. 1-2. In FIG. 1-2, the ordinate refers to the amount of the bound target substance (unit: RU) while the abscissa refers to the time (sec).

Example 4-3

Figures 1, 2, 3:
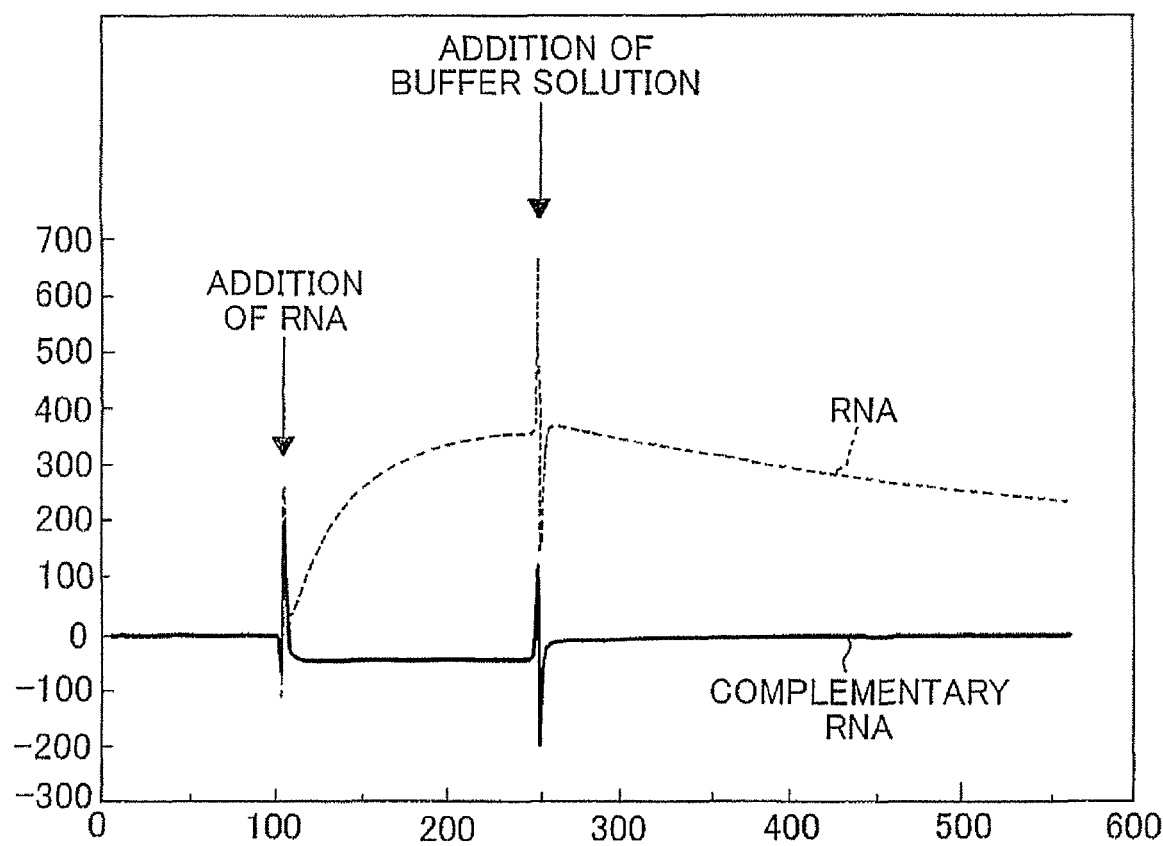
Figure 2:
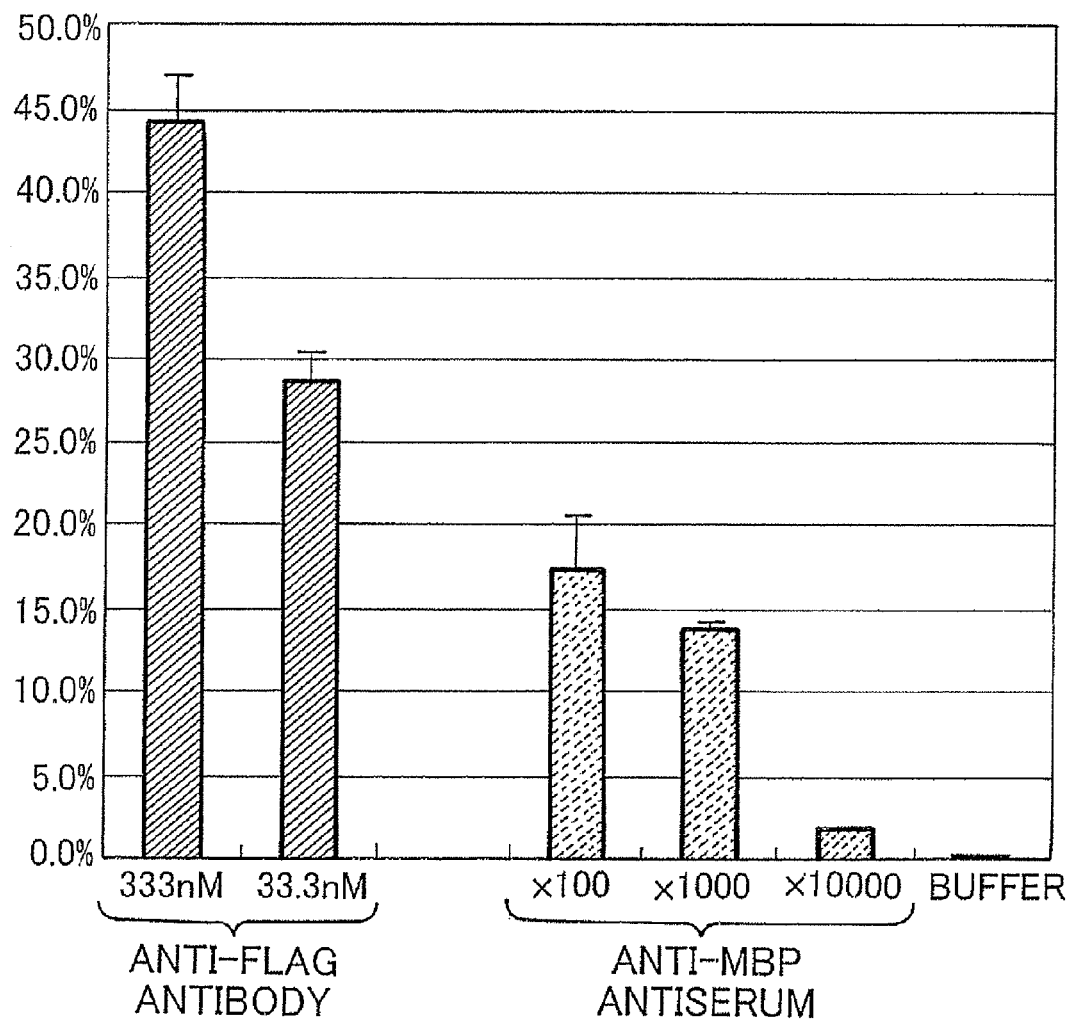

A sensorgram was obtained by utilizing surface plasmon resonance in the same manner as in Example 4-1 except that 10000 RU of anti-GST antibody (rabbit IgG, manufactured by Chemicon) was used in place of 10000 RU of GST. The results are shown in FIG. 1-3. In FIG. 1-3, the ordinate refers to the amount of the bound target substance (unit: RU) while the abscissa refers to the time (sec).

Example 5

The RNAs (20 nM) set forth in SEQ ID NOS: 1 to 5, and the materials (100 nM each) shown in "Material List" below, were incubated in a binding buffer, and then, their binding strength was measured in accordance with the methods described in "Radiolabeling" and "Binding Experiment" below. The results are shown in Table 3.
[Material List]
(1) Binding buffer only
(2) Bovine serum albumin (manufactured by SIGMA)
(3) Glutathione-S-transferase (derived from *Schistosoma japonicum* and prepared in the laboratory from a vector manufactured GE Ltd. in accordance with a protocol of GE Ltd.) (hereinafter, referred to as GST)
(4) Anti-GST antibody (rabbit IgG, manufactured by Chemicon)
(5) A mixture of GST (100 nM) and anti-GST antibody (100 nM)
(6) Mouse IgG (manufactured by Chemicon)
(7) Goat IgG (manufactured by Chemicon)

TABLE 3

| Material No. | Binding strength (%) | | | | |
| --- | --- | --- | --- | --- | --- |
| | SEQ ID NO. 1 | SEQ ID NO. 2 | SEQ ID NO. 3 | SEQ ID NO. 4 | SEQ ID NO. 5 |
| (1) | 0.2 | 0.4 | 0.3 | 0.3 | 0.3 |
| (2) | 0.5 | 1.0 | 1.0 | 0.4 | 0.9 |
| (3) | 0.7 | 0.6 | 0.6 | 0.4 | 0.6 |
| (4) | 19.1 | 24.6 | 20.9 | 23.4 | 58.1 |
| (5) | 13.6 | 14.2 | 14.4 | 20.7 | 48.8 |
| (6) | 0.6 | 0.5 | 1.8 | 0.5 | 0.5 |
| (7) | 0.8 | 0.7 | 1.0 | 0.3 | 0.3 |

[Radiolabeling]
The double-stranded DNA product was used according to the above-described method of in vitro transcription in the presence of $\alpha$-$^{32}$P-ATP (manufactured by Amersham Bioscience), thereby preparing a radio-labeled in vitro transcript.

[Binding Experiment]
The radio-labeled in vitro transcript and the target substance were incubated in a binding buffer at room temperature for twenty minutes.
The resulting mixture was introduced onto a filter (trade name: MF-membrane filter, manufactured by Millipore) by way of suctioning it with a suction device, and then, the filter was washed with a binding buffer that was 20 times the volume of the mixture. The radiation intensity of the filter obtained in this manner was measured with a Bio-Imaging Analyzer BAS-2500 (using, as an imaging plate, BAS-MS2040 manufactured by Fuji Film Co., Ltd.) manufactured by Fuji Film Co., Ltd. The radiation intensity was visualized with Image Reader (Fuji Film Co., Ltd.), and the obtained data were converted into numerical values with Image Gauge ver. 4.0 (Fuji Film Co., Ltd.).

Example 6

The binding strength was measured in the same manner as in Example 5 except that the RNA in SEQ ID NO: 5 was used in place of the RNAs in SEQ ID NOS: 1 to 5; and 333 nM or 33 nM of rabbit anti-Flag-antibody (IgG fraction), or those prepared by diluting a serum fraction (manufactured by New England Biolab; obtained by immunizing a rabbit with MBP (maltose binding protein)) with a binding buffer at the concentration of 100-, 1000- and 10000-fold, respectively, were used as the materials shown in Example 5. The results are shown in FIG. 2. In FIG. 2, the ordinate shows the percentage of the radiation intensity of the radio-labeled in vitro transcript where the radiation intensity before the "Binding Experiment" is considered as 100%.

Example 7

The binding strength was measured in the same manner as in Example 5 except that the RNA in SEQ ID NO: 5 was used in place of the RNAs in SEQ ID NOS: 1 to 5; and those obtained by diluting an IgG fraction in serum (manufactured by Chemicon; obtained by immunizing a rabbit with GST) with a buffer solution (50 mM HEPES, pH 7.4, 150 mM NaCl) to the final concentration of 200 nM, 100 nM, 50 nM and 25 nM, respectively, were used as the materials shown in Example 5. The results are shown in FIG. 3. In FIG. 3, the ordinate refers to the percentage of the radiation intensity of the radio-labeled in vitro transcript where the radiation intensity before the "Binding Experiment" is considered as 100% while the lot numbers used in preparing the IgG fraction and antibody concentrations are shown on the abscissa.

The present invention is described above with reference to preferable embodiments thereof. Herein, although the present invention is described with reference to specific examples, it is evident that these examples can be modified and altered in various ways without departure from the broad purport and scope defined in the accompanying claims. That is, the present invention should not be construed as being limited by the specific examples and the accompanying drawings.

The invention claimed is:

1. An isolated or purified RNA molecule comprising the polynucleotide sequence of any one of SEQ ID NOs: 1-5 wherein the binding constant ($K_D$) of said RNA molecule to the rabbit IgG antibody is $1.18 \times 10^{-7}$ (M) or less.

2. The RNA molecule according to claim 1, which comprises the polynucleotide sequence of SEQ ID NO: 1.

3. The RNA molecule according to claim 1, which comprises the polynucleotide sequence of SEQ ID NO: 2.

4. The RNA molecule according to claim 1, which comprises the polynucleotide sequenceof SEQ ID NO: 3.

5. The RNA molecule according to claim 1, which comprises the polynucleotide sequence of SEQ ID NO: 4.

6. The RNA molecule according to claim 1, which comprises the polynucleotide sequence of SEQ ID NO: 5.

* * * * *